US011583481B2

(12) United States Patent
Hoover

(10) Patent No.: US 11,583,481 B2
(45) Date of Patent: Feb. 21, 2023

(54) DENTIFRICE FORMULATIONS AND METHODS OF ORAL CARE

(71) Applicant: Reoxcyn, LLC, Pleasant Grove, UT (US)

(72) Inventor: Andrew Hoover, Pleasant Grove, UT (US)

(73) Assignee: REOXCYN, LLC, Pleasant Grove, UT (US)

( * ) Notice: Subject to any disclaimer, the term of this patent is extended or adjusted under 35 U.S.C. 154(b) by 0 days.

(21) Appl. No.: 16/209,590

(22) Filed: Dec. 4, 2018

(65) Prior Publication Data
US 2019/0328635 A1 Oct. 31, 2019

Related U.S. Application Data

(63) Continuation of application No. 15/408,203, filed on Jan. 17, 2017, now abandoned.

(60) Provisional application No. 62/446,654, filed on Jan. 16, 2017.

(51) Int. Cl.
A61K 8/20 (2006.01)
A61K 8/25 (2006.01)
A61K 8/46 (2006.01)
A61K 8/24 (2006.01)
A61Q 11/00 (2006.01)

(52) U.S. Cl.
CPC ............... A61K 8/20 (2013.01); A61K 8/24 (2013.01); A61K 8/25 (2013.01); A61K 8/463 (2013.01); A61Q 11/00 (2013.01)

(58) Field of Classification Search
CPC . A61Q 11/00; A61K 8/20; A61K 7/20; C11D 3/39
USPC ....................................... 424/53; 252/186.38
See application file for complete search history.

(56) References Cited

U.S. PATENT DOCUMENTS

| | | | |
|---|---|---|---|
| 3,886,266 A | 5/1975 | Goldman et al. | |
| 4,956,184 A | 9/1990 | Kross | |
| 6,114,398 A | 9/2000 | Ratcliff | |
| 7,108,997 B2 | 9/2006 | Kettle | |
| 8,518,382 B2 | 8/2013 | Speronello et al. | |
| 8,673,297 B2 | 3/2014 | Speronello et al. | |
| 8,784,900 B2 | 7/2014 | Northey | |
| 9,072,793 B2 | 7/2015 | Eckert et al. | |
| 9,175,141 B2 | 11/2015 | Wray et al. | |
| 9,474,768 B1 | 10/2016 | Richards | |
| 2004/0213698 A1* | 10/2004 | Tennakoon | A61K 8/20 422/37 |
| 2005/0089537 A1 | 4/2005 | Birnholz | |
| 2006/0060819 A1 | 3/2006 | Jung | |
| 2007/0172412 A1 | 7/2007 | Hratko et al. | |
| 2007/0281008 A1 | 12/2007 | Lin et al. | |
| 2008/0003171 A1 | 1/2008 | Smith et al. | |
| 2008/0008621 A1 | 1/2008 | Masahiro et al. | |
| 2009/0028811 A1 | 1/2009 | Potter | |
| 2009/0068122 A1 | 3/2009 | Shira et al. | |
| 2009/0148342 A1* | 6/2009 | Bromberg | A61L 2/23 422/37 |
| 2009/0169646 A1 | 7/2009 | Bosch et al. | |
| 2010/0012132 A1 | 1/2010 | Harrison et al. | |
| 2012/0046556 A1 | 2/2012 | Block | |
| 2012/0052022 A1 | 3/2012 | Dayanim | |
| 2013/0164228 A1 | 6/2013 | Stanislav et al. | |
| 2013/0168260 A1 | 7/2013 | Scherson et al. | |
| 2014/0044800 A1 | 2/2014 | Robinson | |
| 2014/0328946 A1 | 11/2014 | Northey | |
| 2015/0017257 A1 | 1/2015 | Megumi et al. | |
| 2015/0030546 A1 | 1/2015 | O'Malley | |
| 2015/0009901 A1 | 4/2015 | Hoover | |
| 2015/0093451 A1 | 4/2015 | Neiman | |
| 2015/0118180 A1 | 4/2015 | Hoover | |
| 2015/0246131 A1 | 9/2015 | Romanoschi et al. | |
| 2015/0250704 A1 | 9/2015 | Romanoschi et al. | |
| 2016/0296434 A1 | 10/2016 | Fei et al. | |

FOREIGN PATENT DOCUMENTS

| | | | | |
|---|---|---|---|---|
| CN | 102167997 | | 6/2013 | |
| EP | 1886664 | | 2/2008 | |
| WO | WO 9934773 | | 7/1999 | |
| WO | WO2007078074 | * | 7/2007 | ............... A61K 8/21 |
| WO | WO 2010004699 | | 1/2010 | |
| WO | WO 2015002932 | | 3/2015 | |

OTHER PUBLICATIONS

Chen, "Novel technologies for the prevention and treatment of dental caries: a patent survey", Expert Opin Ther Pat. May 2010; 20(5): 681-694.

Prasanth, "Antimicrobial Efficacy of Different Toothpastes and Mouthrinses: An In Vitro Study", Dent Res J (Isfahan), 2011 Spring, 8(2); 85-94.

Storhagen et al., "Dentifrices and Mouthwashes Ingredients and Their Use." 2003; Sem 1 0.sem v99; pp. 1-49.

* cited by examiner

Primary Examiner — Walter E Webb
(74) Attorney, Agent, or Firm — Knobbe, Martens, Olson & Bear LLP

(57) ABSTRACT

Oral care compositions are disclosed. The compositions include hypochlorous acid in combination with one or more of a rheology agent, an abrasive, a surfactant, a buffer, or an inorganic compound. Methods of using and making the dentifrice compositions are also disclosed.

13 Claims, No Drawings

DENTIFRICE FORMULATIONS AND METHODS OF ORAL CARE

RELATED APPLICATIONS

This application is a continuation application of U.S. Ser. No. 15/408,203, filed Jan. 17, 2017, which claims the benefit of priority to U.S. Provisional Patent Application No. 62/446,654, filed Jan. 16, 2017, the disclosures of which are incorporated by reference herein in their entireties.

FIELD OF THE DISCLOSURE

The present disclosure relates generally to oral care compositions and methods of use. More specifically, the present disclosure is related to oral care compositions having hypochlorite, or acids or salts thereof, and one or more of a rheology agent, an abrasive, a surfactant, or a buffer, and methods of using the compositions for the care of the oral cavity.

BACKGROUND

General health and well-being are connected to the health of the oral cavity. Poor oral health affects millions of individuals, and results in symptoms ranging from halitosis (bad breath), tooth decay, and gum disease, to general health issues such as heart disease, stroke, poorly controlled diabetes, and preterm birth.

Various methods and oral health compositions have been employed for maintenance of good oral health and for prevention of diseases or disorders connected with poor oral hygiene. These may include proper oral hygiene through the use of tooth polishing, flossing, and regular dental checkups and the use of various compositions, such as toothpastes and oral rinses.

SUMMARY

The present disclosure describes oral care compositions for use in oral hygiene. Also described are methods of making and using the oral care compositions formulations. The formulations and methods of using the formulations described herein can be used for caring for the oral cavity, for whitening of teeth, and for the treatment or prevention of microbial growth in the oral cavity.

Accordingly, in some embodiments is provided an oral care composition. In some embodiments, the oral care composition includes hypochlorite, or acids or salts thereof, a rheology agent, an abrasive, a surfactant, and a buffer, or combinations thereof.

In some embodiments, hypochlorite is present as hypochlorous acid. In some embodiments, hypochlorous acid is present in an amount of about 10 to about 300 ppm. In some embodiments, the hypochlorous acid is present in an amount of 5, 10, 15, 20, 25, 30, 35, 40, 45, 50, 55, 60, 65, 70, 75, 80, 85, 90, 95, 100, 125, 150, 175, 200, 225, 250, 275, 300, or 350 ppm, or an amount within a range defined by any two of the aforementioned values. In some embodiments, hypochlorous acid is present in an amount of about 75 ppm.

In some embodiments, the oral care composition includes a rheology agent. In some embodiments, the rheology agent is sodium magnesium silicate. In some embodiments, sodium magnesium silicate is present in an amount of about 0.5 to about 10% w/v. In some embodiments, the rheology agent is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, or 15% w/v, or a percent w/v within a range defined by any two of the aforementioned values. In some embodiments, sodium magnesium silicate is present in an amount of about 5% w/v.

In some embodiments, the oral care composition includes an abrasive. In some embodiments, the abrasive is hydrated silica. In some embodiments, the hydrated silica is present in an amount of about 10 to about 30% w/v. In some embodiments, the abrasive is present in an amount of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35% w/v, or a percent w/v within a range defined by any two of the aforementioned values. In some embodiments, the hydrated silica is present in an amount of about 18% w/v.

In some embodiments, the oral care composition includes a surfactant. In some embodiments, the surfactant is sodium coco sulfate (SCS). In some embodiments, SCS is present in an amount of about 0 to about 5% w/v. In some embodiments, the surfactant is present in an amount of 0, 1, 2, 3, 4, 5, 6, 7, 8, 9, or 10% w/v, or a percent w/v within a range defined by any two of the aforementioned values. In some embodiments, SCS is present in an amount of about 1% w/v.

In some embodiments, the oral care composition includes a buffer. In some embodiments, the buffer is a phosphate buffer, including, for example, potassium phosphate dibasic, tri-potassium phosphate, or sodium phosphate. In some embodiments, the buffer is present in an amount of about 0 to about 5% w/v. In some embodiments, the buffer is present in an amount of 0, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, or 10% w/v, or a percent w/v within a range defined by any two of the aforementioned values. In some embodiments, the buffer is present in an amount of about 1% w/v.

In some embodiments is provided an oral care composition, including hypochlorous acid, sodium magnesium silicate, hydrated silica, and optionally including one or more of SCS and phosphate buffer.

In some embodiments, the oral care composition is provided having hypochlorous acid in an amount of about 75 ppm, sodium magnesium silicate in an amount of about 5% w/v, hydrated silica in an amount of about 18% w/v, SCS in an amount of about 1% w/v, and phosphate buffer in an amount of about 1% w/v.

In some embodiments, the oral care composition formulated as a paste. In some embodiments, the oral care composition is a toothpaste.

In some embodiments is provided a method of making an oral care composition. In some embodiments, the method of making the oral care composition includes providing a solution having hypochlorous acid, sodium magnesium silicate, SCS, and phosphate buffer, providing a paste having hydrated silica, and mixing the ingredients to form an oral care composition.

In some embodiments is provided a method for caring for an oral cavity. In some embodiments, caring for an oral cavity includes applying an oral care composition as described herein to the oral cavity. In some embodiments, applying the oral care composition includes polishing a tooth surface.

In some embodiments, caring for the oral cavity includes cleansing a tooth surface, whitening a tooth surface, killing or inhibiting the growth or proliferation of microbes, inhibiting biofilm formation in the oral cavity, reducing plaque formation, reducing or inhibiting gingivitis, reducing or inhibiting periodontitis, reducing or inhibiting the formation of dental caries, reducing or inhibiting pre-carious lesions of the enamel, reducing or inhibiting halitosis, or promoting body health, or combinations thereof.

In some embodiments is provided an oral care composition, including hypochlorous acid and calcium chloride. In some embodiments, hypochlorous acid is present in an amount of about 10 to about 300 ppm. In some embodiments, the hypochlorous acid is present in an amount of 5, 10, 15, 20, 25, 30, 35, 40, 45, 50, 55, 60, 65, 70, 75, 80, 85, 90, 95, 100, 125, 150, 175, 200, 225, 250, 275, 300, or 350 ppm, or an amount within a range defined by any two of the aforementioned values. In some embodiments, hypochlorous acid is present in an amount of about 27 ppm.

In some embodiments, the calcium chloride is present in an amount of 0.1% to 5% w/v. In some embodiments, the calcium chloride is present in an amount of 0.05, 0.01, 0.15, 0.2, 0.3, 0.4, 0.5, 0.6, 0.7, 0.8, 0.9, 1, 2, 3, 4, 5, 6, 7, 8, 9, or 10% w/v, or a percent w/v within a range defined by any two of the aforementioned values. In some embodiments, the calcium chloride is present in an amount of about 1% w/v. In some embodiments, the oral care composition is formulated as an oral rinse, an oral spray, or a mouth wash.

In some embodiments is provided a method for caring for an oral cavity using an oral care composition of hypochlorous acid and calcium chloride. In some embodiments, the method of caring for an oral cavity includes applying the oral care composition to the oral cavity. In some embodiments, applying the oral care composition includes rinsing the oral cavity with the oral care composition. In some embodiments, caring for the oral cavity includes cleansing a tooth surface, whitening of a tooth surface, killing or inhibiting the growth or proliferation of microbes, or inhibiting biofilm formation in the oral cavity, reducing plaque formation, reducing or inhibiting gingivitis, reducing or inhibiting periodontitis, reducing or inhibiting the formation of dental caries, reducing or inhibiting pre-carious lesions of the enamel, reducing or inhibiting halitosis, or promoting body health, or combinations thereof.

In some embodiments is provided a method of caring for an oral cavity. In some embodiments, the method includes providing an oral paste as described herein and providing an oral rinse as described herein. In some embodiments, the oral paste is a composition including hypochlorous acid, sodium magnesium silicate, hydrated silica, and optionally including one or more of SCS and phosphate buffer. In some embodiments, the oral paste is a composition including hypochlorous acid in an amount of about 75 ppm, sodium magnesium silicate in an amount of about 5% w/v, hydrated silica in an amount of about 18% w/v, SCS in an amount of about 1% w/v, and phosphate buffer in an amount of about 1% w/v. In some embodiment, the oral rinse is a composition including calcium chloride and hypochlorous acid. In some embodiments, the oral rinse is a composition including calcium chloride in an amount of about 1% w/v and hypochlorous acid in an amount of about 27 ppm.

DETAILED DESCRIPTION

It will be readily understood that the aspects of the present disclosure, as generally described herein, can be arranged, substituted, combined, separated, and designed in a wide variety of different configurations, all of which are explicitly contemplated herein.

Oral care compositions, including toothpaste or mouthwash compositions are described herein. The oral care compositions are useful for caring for an oral cavity. In some embodiments is provided a method of caring for an oral cavity including applying the oral care compositions as described herein to the oral cavity. In some embodiments, the oral care composition may be used alone or in combination with other compositions used for oral care, including other toothpastes or mouthwashes. In some embodiments, oral care compositions may be useful for cleansing a tooth surface, whitening of a tooth surface, killing or inhibiting the growth or proliferation of microbes, or inhibiting biofilm formation in the oral cavity, reducing plaque formation, reducing or inhibiting gingivitis, reducing or inhibiting periodontitis, reducing or inhibiting the formation of dental caries, reducing or inhibiting pre-carious lesions of the enamel, reducing or inhibiting halitosis, or promoting body health, or combinations thereof.

Unless defined otherwise, technical and scientific terms used herein have the same meaning as commonly understood by one of ordinary skill in the art to which the present disclosure belongs. For purposes of the present disclosure, the following terms are defined below.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. When a value is preceded by the term about, the component is not intended to be limited strictly to that value, but it is intended to include amounts that vary from the value.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In some embodiments, the "purity" of any given agent (for example, hypochlorous acid or a buffer) in a composition may be specifically defined. For instance, certain compositions may include, for example, an agent that is at least 80, 85, 90, 91, 92, 93, 94, 95, 96, 97, 98, 99, or 100% pure, including all decimals in between, as measured, for example and by no means limiting, by analytical chemistry techniques.

As used herein, the terms "function" and "functional" and the like refer to a biological, chemical, mechanical, or therapeutic function.

As used herein, the term "oral care composition" refers to a dentifrice composition or formulation that is used for the care or maintenance of the health of the oral cavity. In some embodiments, an oral care composition provides prophylactic care of the oral cavity. In some embodiment, an oral care composition provides beneficial effects to existing oral deficiencies. In some embodiments, an oral care composition is a composition that is used for oral hygiene, either for the care, maintenance, treatment, prevention, inhibition, amelioration, or benefit of the oral cavity. In some embodiments, the oral care compositions described herein have antimicrobial properties, capable of removing microorganisms from the oral cavity, and capable of preventing growth and proliferation of microorganisms in the oral cavity. In some embodiments, the oral care composition is applied to the oral cavity as a paste or as a rinse. In some embodiments, the oral care composition is formulated as a paste, a rinse, a cream, a gel, a spray, a lozenge, a tablet, a strip, or similar composition for use in oral hygiene. As used herein, the term "oral cavity" refers to the mouth or mouth region, including the palate, the interior of the lips, the teeth, the tongue, the throat, the gums and the interior of the jaws.

In some embodiments, the oral care compositions are used alone by direct application of the oral care compositions to the oral cavity. In some embodiments, the oral care compositions described herein are used in combination with other products including other dental hygiene products. For example, in some embodiments, an oral care composition as described herein may be used in combination with a toothpaste or a toothbrush. In some embodiments, the oral care compositions may be used together with a mouth guard or dentistry tray or with floss or strips. In some embodiments, the oral care compositions may be used in combination with any other paste, rinse, cream, gel, spray, lozenge, tablet, strip, or similar composition used in oral hygiene.

"Hypochlorous acid", as used herein, refers to a weak acid having the chemical formula HClO. Hypochlorous acid is also known as chloric (I) acid, chloranol, or hydroxidochlorine. Salts of hypochlorite are also referred to herein and can include sodium hypochlorite (NaClO), calcium hypochlorite ($Ca(ClO)_2$), or potassium hypochlorite (KClO). As described herein, hypochlorous acid and hypochlorite are used as killing agents, cleansing agents, disinfectants, bleaching agents, whitening agents, antibacterial agents, sanitizers, and/or preservatives. Hypochlorite, or acids and salts thereof, may be used in the oral care compositions of the present disclosure at an amount of about 0.5%, 1%, 5%, 10%, 15%, 20%, 25%, 30%, 40%, 50%, or greater w/v %, or within a range defined by any two of the aforementioned amounts. In some embodiments, the w/v % of hypochlorite or an acid or salt thereof is about 25% w/v. In some embodiments, the hypochlorite salt or hypochlorous acid is added directly to an oral care composition. In some embodiments, the final amount of hypochlorous acid is less than, greater than, or equal to about 10, 15, 20, 25, 30, 35, 40, 45, 50, 55, 60, 65, 70, 75, 80, 85, 90, 95, 100, 120, 150, 175, 200, 300 ppm or within a range defined by any two of the aforementioned amounts. In some embodiments, the amount of hypochlorous acid in the oral care composition is between about 50 to about 100 ppm. In some embodiments, the amount of hypochlorous acid in the oral care composition is about 75 ppm. In some embodiments, the amount of hypochlorous acid in the oral care composition is about 27 ppm.

In some embodiments, hypochlorous acid is added to the oral care composition as a hypochlorite solution. In some embodiments, the hypochlorite solution is prepared from hypochlorite salt or hypochlorous acid. In some embodiments, the solution of hypochlorite is prepared by passing a sodium chloride solution through electrolysis. In some embodiments, the sodium chloride solution is a 0.1%, 0.15%, 0.2%, 0.25%, 0.3%, 0.35%, 0.4% or greater w/v % or within a range defined by any two of the aforementioned amounts. In some embodiments, the sodium chloride is 0.28%, and the resulting hypochlorite solution is 300 ppm. In some embodiments, the hypochlorite solution is added to the oral care composition in an amount of about 0.5%, 1%, 5%, 10%, 15%, 20%, 25%, 30%, 40%, 50% or greater w/v %, or within a range defined by any two of the aforementioned amounts. In some embodiments, the solution includes, for example, about 300 ppm hypochlorite is added to an oral care composition in an amount of about 25% w/v.

As used herein, the term "rheology agent" refers to a substance that modulates the viscosity of the oral care composition, without modifying other properties of the composition. In some embodiments, the rheology agent acts as a thickener by increasing the viscosity of the oral care composition. In some embodiments, the rheology agent can include sodium magnesium silicate, a silicate of sodium and magnesium. In some embodiments, sodium magnesium silicate is a synthetic silicate clay, having magnesium and sodium silicate. It is used as a binder and bulking agent in cosmetics and personal care products, in part because of its ability to absorb water. Sodium magnesium silicate is effective in slowing the decomposition of formulas, and can prevent premature darkening of compositions and prevent premature development of a foul odor, thereby improving the shelf life of cosmetic compositions. In some embodiments, the sodium magnesium silicate is Laponite, including for example, XLG Laponite or Laponite XL21. The rheology agent may be used in the oral care composition in an amount of about 0.1%, 0.25%, 0.5%, 0.75%, 1%, 1.5%, 2%, 2.5%, 3%, 3.5%, 4%, 4.5%, 5%, 6%, 7%, 10%, 15%, or greater w/v %, or in an amount within any two of the aforementioned values or between a range defined by these values. In some embodiments, the amount of rheology agent is about 5% w/v.

As used herein, the term "abrasive" refers to a component or substance of the oral care composition that is capable of abrading or scraping a surface. In some embodiments, the abrasive may include one or more type of abrasive particulates, including for example, sodium bicarbonate, calcium phosphate, calcium pyrophosphate, calcium sulfate, silica, iron oxide, aluminum oxide, perlite, or plastic particles (such as polyethylene). In some embodiments, the silica includes hydrated silica, precipitated silica, or silica gel. The abrasive may be used in the oral care composition in an amount of about 0.1%, 0.25%, 0.5%, 0.75%, 1%, 1.5%, 2%, 2.5%, 3%, 3.5%, 4%, 4.5%, 5%, 6%, 7%, 10%, 15%, 20% 25%, 30% or greater w/v %, or in an amount within any two of the aforementioned values or between a range defined by these values. In some embodiments, the amount of abrasive is about 18% w/v.

As used herein, the term "surfactant" refers to a surface active compound. A surface active compound is a compound or substance that lowers the surface tension of a material containing the substance by adsorption on the interface. A surfactant can be a pure chemical compound or a mixture of different chemical compounds. Surfactants can include lecithin, monoglycerides, monostearates, ethoxylates, sulfates, and sulfates of ethoxylates such as sodium dodecyl sulfate (SDS or sodium lauryl sulfate), sodium laureth sulfate (SLES), sodium coco sulfate (SCS). The surfactant may be used in the oral care composition in an amount of about 0.1%, 0.25%, 0.5%, 0.75%, 1%, 1.5%, 2%, 2.5%, 3%, 3.5%, 4%, 4.5%, 5%, 6%, 7%, 10%, 15%, or greater w/v %, or in an amount within any two of the aforementioned values or between a range defined by these values. In some embodiments, the amount of surfactant is about 1% w/v.

As used herein, the term "buffer" refers to solutions that resist changes in pH by the action of its conjugate acid-base range. The buffer may be used as an initial solution in the manufacture of the oral care composition, and then modified for the specified use, such as for us in a gel, a paste, a cream, a spray, a rinse, or other composition. Examples of buffers can include citrate, phosphate, acetate, or other mineral acid or organic acid buffers, or combinations thereof. In some embodiments, the buffer is a phosphate buffer, such as sodium phosphate monobasic, potassium phosphate dibasic, tri potassium phosphate, or other salts of phosphate. As described herein, the buffer may be used for adjustment of pH, as a thickening agent by the introduction of ions, or as a buffer. The buffer may be used in the oral care composition in an amount of about 0.05%, 0.1%, 0.2%, 0.3%, 0.4%, 0.5%, 1%, 1.5%, 2%, 2.5%, 3%, 3.5%, 4%, 4.5%, 5%, 6%, 7%, 10%, 15%, or greater w/v %, or in an amount within any two of the aforementioned values. In some embodiments, the amount of sodium phosphate is about 1% w/v.

In some embodiments, an oral care compositions includes hypochlorous acid in an amount from about 10 to about 300 ppm, sodium magnesium silicate in an amount from about 0.5% to about 10% w/v, hydrated silica in an amount of about 10% to about 30% w/v, SCS in an amount of about 0.1% to about 5% w/v, and a phosphate buffer in an amount of about 0.1% to about 5%. In some embodiments, the oral care composition includes about 75 ppm hypochlorous acid, about 5% w/v sodium magnesium silicate, about 18% w/v hydrated silica, about 1% w/v SCS, and about 1% w/v phosphate buffer.

In some embodiments, the oral care composition includes hypochlorous acid and calcium chloride ($CaCl_2$)). In some embodiments, the calcium chloride based oral care composition is formulated as a solution for use as an oral rinse, mouth wash, or oral spray. In some embodiments, hypochlorous acid is present in an amount from about 10 to about 300 ppm. In some embodiments, $CaCl_2$) is present in an amount of about 0.5% to about 5% w/v. In some embodiments, the oral care composition includes about 27 ppm hypochlorous acid and about 1% w/v $CaCl_2$).

As used herein, the pH of the oral care composition is the numerical scale to specify the acidity or basicity of the formulation. In some embodiments, the pH of the formulation is about 5.0, 5.5, 6.0, 6.5, 6.6, 6.7, 6.8, 6.9, 7.0, 7.1, 7.2, 7.3, 7.4, 7.5, 7.6, 7.7, 7.8, 7.9, 8.0, or 8.5, or within a ranged defined by any two of the aforementioned values. In some embodiments, the pH of the oral care composition is in a range from about 6.5 to about 7.5.

The oral care compositions described herein may further include an additive known in the art. Exemplary additives include sweeteners, preservatives, emulsifiers, detergents, emollients, moisturizers, humectants, pigments, dyes, pearlescent compounds, effervescent agents, calcium, fluoride, titanium dioxide coated mica, colorants, fragrances, flavorants, biocides, alpha hydroxy acids, antioxidants, antimicrobial agents, anti-fungal agents, exfoliants, hormones, enzymes, medicinal compounds, vitamins, salts, electrolytes, alcohols, polyols, polypropylene glycol, polyisobutene, polyoxyethylene, behenic acid, behenyl, sugar-alcohols, botanical extracts, surfactants, organic oils, waxes, alkaline or acidic or buffering agents, film formers, thickening agents, hyaluronic acid, fumed silica, talc, kaolin, starch, modified starch, mica, nylon, clay, bentonite, organomodified clays and combinations thereof.

In some embodiments is provided a method of making the oral care composition. In some embodiments, the method includes providing a solution of hypochlorous acid in combination with a rheology agent, a surfactant, and a buffer. In some embodiments, the method includes providing a paste, gel, cream, or second solution that contains an abrasive. In some embodiments, the hypochlorous acid solution is mixed with the abrasive solution, paste, gel, or cream to form an oral care composition. In some embodiments, the oral care composition is formulated as a paste, including as a toothpaste, a polish, a whitener, a gel, a cream, a lozenge, a tablet, a strip, a spray, a rinse, or a wash.

In some embodiments, the oral care composition is prepared by mixing a solution of hypochlorous acid with a solution of calcium chloride to form a calcium chloride based oral care composition. In some embodiments, the oral care composition is prepared by mixing a solution of hypochlorous acid with solid calcium chloride.

In some embodiments, water and/or buffer is provided in an amount to make up the balance of the oral care composition, and is provided in an amount of about 20%, 30%, 40%, 45%, 50%, 55%, 56%, 57%, 58%, 59%, 60%, 61%, 61.55%, 62%, 62.5%, 63%, 65%, 70%, 75%, 80%, or 90% w/v or within a range defined by any two of the aforementioned amounts.

In some embodiments is provided a method of using the oral care compositions. In some embodiments, the method includes providing the oral care composition and applying the oral composition. In some embodiments, the oral care composition is provided as a ready-to-use formulation that includes hypochlorous acid, a rheology agent, an abrasive, a surfactant, and a buffer. In some embodiments, the oral care composition is provided in portions, or in separate components, and further additions and/or mixing is required prior to use. In some embodiments, the oral care composition is applied to the oral cavity of a user. In some embodiments, the oral care composition is applied as a paste, a toothpaste, a whitener, a polishing agent, a wash, a rinse, a spray, a lozenge, or a tablet. In some embodiments, the oral care composition is applied multiple times daily, once daily, multiple times weekly, once weekly, multiple times monthly, or once monthly, or within a time frame defined by any two of the aforementioned time frames. In some embodiments, the oral care composition is applied liberally. In some embodiments, the oral care composition is applied meagerly.

In some embodiments, the oral care composition as disclosed herein is useful for disinfecting a surface, including the surface of the oral cavity, such as the surface of the mouth or mouth region, the palate, the interior of the lips, the teeth, the tongue, the throat, the gums, or the interior of the jaws. In some embodiments, the oral care composition described herein is used in a healthcare facility setting, such as at a dental office or in a hospital. In some embodiments, the oral care composition includes hypochlorous acid, a rheology agent, an abrasive, a surfactant, and a buffer.

In some embodiments is provided a method of using an oral care composition for cleansing a tooth surface, whitening a tooth surface, killing or inhibiting the growth or proliferation of microbes, inhibiting biofilm formation in the oral cavity, reducing plaque formation, reducing or inhibiting gingivitis, reducing or inhibiting the formation of dental caries, reducing or inhibiting pre-carious lesions of the enamel, reducing or inhibiting halitosis, or promoting body health.

In some embodiments, cleansing the oral cavity includes the removal of particulate material from the surface of the oral cavity, including from the surface of the mouth or mouth region, including the palate, the interior of the lips, the teeth, the tongue, the throat, the gums and the interior of the jaws. In some embodiments, the oral care composition is applied directly to the oral cavity. In some embodiments, the use of an oral care composition includes application of the composition on a toothbrush, which is used to polish the surface of the teeth, or to cleanse the surface of oral cavity. In some embodiments, the oral care composition is applied to a mouth guard or dentistry tray, which is then applied to the oral cavity for contact with the oral cavity or teeth.

In some embodiments, cleansing a tooth surface includes the removal of dental plaque or dental calculus (tartar) from the surface of a tooth. Dental plaque is produced by the attachment and proliferation of a variety of bacteria on the surface of a tooth. The bacteria form a biofilm that can give rise to dental calculus, tooth decay, gingivitis, periodontitis, and general health decline. Such bacteria may include *Streptococcus mutans* or *Actinomyces naeslundii*. Application of the oral care composition eliminates the pathogens involved in dental plaque formation and dental tartar formation. Thus, the application of the oral care compositions eliminates microbial plaque formation, reduces or prohibits the formation of microbial biofilm formation, reduces or inhibits dental calculus, reduces or inhibits gingivitis, periodontitis, dental caries, or precarious lesion of the enamel. Furthermore, the application of the oral care compositions provided herein promotes general health, including reducing the risk of heart disease, stroke, poorly controlled diabetes, and preterm birth associated with poor oral hygiene.

In some embodiments, the oral care compositions are applied for the reduction or inhibition of halitosis. In some embodiments, the oral care compositions are applied alone or in combination with one or more oral care products.

In some embodiments, the oral care compositions are applied to the oral cavity for the whitening of teeth. In some embodiments, the hypochlorite present in the oral care compositions acts as a bleach to whiten the surface of teeth. The composition may be formulated as a gel, gum, rinse, paste, paint-on film, strip, or spray or other formulation for application of the composition to the surface of the teeth. The composition may be directly applied to the surface of the teeth, or may be applied in combination with a mouth guard, a dental tray, a brush, floss, or a strip. The composition may be used alone or in combination with other bleaching agents, whitening agents, or other additives.

In some embodiments, the oral care composition as disclosed herein is useful as a sanitizer or as a dental disinfectant for use with dental instruments for disinfecting a dental device or instrument prior to, during, or after use.

The invention is generally disclosed herein using affirmative language to describe the numerous embodiments. The invention also includes embodiments in which subject matter is excluded, in full or in part, such as substances or materials, method steps and conditions, protocols, or procedures.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention, as it is described herein above and in the claims.

Example 1

Preparation of Oral Care Paste

The following example demonstrates a method of preparing an oral care paste.

An oral care paste was prepared with the ingredients as provided in Table 1. Hypochlorite or a salt or acid thereof was added to water, sodium coco sulfate, XLG Laponite, potassium phosphate dibasic, and hydrated silica in the preparation of an oral care paste composition.

TABLE 1

| Oral Care Paste | |
|---|---|
| Ingredient | Quantity |
| Hypochlorite | 75 ppm |
| Sodium Coco Sulfate (SCS) | 1% w/v |
| XLG Laponite (sodium magnesium silicate) | 5% w/v |
| Potassium Phosphate Dibasic | 1% w/v |
| Hydrated Silica | 18% w/v |
| Water | balance |

The oral care paste described in Table 1 is useful for polishing or cleansing a surface of a tooth. The composition may be used alone in or in combination with other oral hygiene products. Furthermore, the composition may be applied directly to the oral cavity or may be applied with an oral hygiene product, such as with a toothbrush, a dental tray, floss, or with strips. The oral care paste may be formulated as a toothpaste, a polish, a whitener, a gel, a cream, or other paste. The oral care paste may additionally include an additive including sweeteners, preservatives, emulsifiers, detergents, emollients, moisturizers, humectants, pigments, dyes, pearlescent compounds, effervescent agents, calcium, fluoride, titanium dioxide coated mica, colorants, fragrances, flavorants, biocides, alpha hydroxy acids, antioxidants, anti-microbial agents, anti-fungal agents, exfoliants, hormones, enzymes, medicinal compounds, vitamins, salts, electrolytes, alcohols, polyols, polypropylene glycol, polyisobutene, polyoxyethylene, behenic acid, behenyl, sugar-alcohols, botanical extracts, surfactants, organic oils, waxes, alkaline or acidic or buffering agents, film formers, thickening agents, hyaluronic acid, fumed silica, talc, kaolin, starch, modified starch, mica, nylon, clay, bentonite, organo-modified clays and combinations thereof.

Example 2

Preparation of Oral Care Rinse

The following example demonstrates a method of preparing an oral care rinse.

An oral care rinse was prepared with the ingredients as provided in Table 2. Hypochlorite or a salt or acid thereof was added to water and calcium chloride in the preparation of an oral care rinse composition.

TABLE 2

| Oral Care Rinse | |
|---|---|
| Ingredient | Quantity |
| Calcium Chloride (CaCl$_2$) | 1% w/v |
| Hypochlorite | 27 ppm |
| Water | balance |

The oral care rinse described in Table 2 is useful for cleansing an oral cavity. The composition may be used alone in or in combination with other oral hygiene products. Furthermore, the composition may be applied directly to the oral cavity or may be applied with an oral hygiene product, such as with a toothbrush, a dental tray, floss, or with strips. The oral care rinse may be formulated as a polisher, a whitener, a mouthwash, a spray, an oral rinse, or a liquid floss. The oral rinse may be formulated for use for cleansing the surface of teeth, gums, tongue, palate, interior of the lips, or throat, for whitening or for polishing of the teeth, for preventing, ameliorating, treating, or decreasing bacterial growth, for reducing, eliminating, preventing, or ameliorating the effects of halitosis, or for other oral hygiene needs. The oral care rinse may additionally include an additive including sweeteners, preservatives, emulsifiers, detergents, emollients, moisturizers, humectants, pigments, dyes, pearlescent compounds, effervescent agents, calcium, fluoride, titanium dioxide coated mica, colorants, fragrances, flavorants, biocides, alpha hydroxy acids, antioxidants, antimicrobial agents, anti-fungal agents, exfoliants, hormones, enzymes, medicinal compounds, vitamins, salts, electrolytes, alcohols, polyols, polypropylene glycol, polyisobutene, polyoxyethylene, behenic acid, behenyl, sugar-alcohols, botanical extracts, surfactants, organic oils, waxes, alkaline or acidic or buffering agents, film formers, thickening agents, hyaluronic acid, fumed silica, talc, kaolin, starch, modified starch, mica, nylon, clay, bentonite, organo-modified clays and combinations thereof.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A kit, comprising:
    a first oral care composition consisting of:
        an electrolyzed saline solution comprising hypochlorous acid present in an amount ranging from about 10 ppm to about 75 ppm,
        sodium magnesium silicate,
        hydrated silica,
        sodium coco sulfate (SCS),
        potassium phosphate dibasic, and
        water;
        wherein the first oral care composition is formulated as a paste, a gel, or a cream; and
    a second oral care composition consisting of:

hypochlorous acid present in an amount ranging from about 10 ppm to about 27 ppm,
calcium chloride, and
water,
wherein the first oral care composition and the second oral care composition have a pH ranging from 5.0 to 7.

2. The kit of claim 1, wherein the hypochlorous acid in the first oral care composition is present in an amount of about 75 ppm.

3. The kit of claim 1, wherein the sodium magnesium silicate is present in an amount of about 0.5 to about 10% w/v.

4. The kit of claim 1, wherein the sodium magnesium silicate is present in an amount of about 5% w/v.

5. The kit of claim 1, wherein the hydrated silica is present in an amount of about 10 to about 30% w/v.

6. The kit of claim 1, wherein the SCS is present in an amount of about 0.1 to about 5% w/v.

7. The kit of claim 1, wherein the potassium phosphate dibasic is present in an amount of about 0.1 to about 5% w/v.

8. The kit of claim 1, wherein the first oral care composition consists of hypochlorous acid in an amount of about 75 ppm, sodium magnesium silicate in an amount of about 5% w/v, hydrated silica in an amount of about 18% w/v, SCS in an amount of about 1% w/v, potassium phosphate dibasic in an amount of about 1% w/v, and water in balance.

9. The kit of claim 1, wherein the paste is a toothpaste.

10. The kit of claim 1, wherein the first oral care composition is formulated for application to a strip.

11. The kit of claim 1, wherein the hypochlorous acid in the second oral care composition is present in an amount of about 27 ppm.

12. The kit of claim 1, wherein the calcium chloride is present in an amount of 0.5% to 5% w/v.

13. The kit of claim 1, wherein the second oral care composition is formulated as an oral rinse, an oral spray, or a mouthwash.

* * * * *